United States Patent [19]

Williams

[11] 4,163,526

[45] Aug. 7, 1979

[54] CABLE STORAGE ASSEMBLY FOR SCANNING APPARATUS

[75] Inventor: Anthony M. Williams, Iver, England

[73] Assignee: EMI Limited, Hayes, England

[21] Appl. No.: 827,007

[22] Filed: Aug. 23, 1977

[30] Foreign Application Priority Data

Aug. 21, 1976 [GB] United Kingdom ............... 34938/76

[51] Int. Cl.² .......................................... B65H 75/00
[52] U.S. Cl. ............................................... 242/54 R
[58] Field of Search ............... 242/54 R, 47.04, 47.05, 242/47.08, 47.1, 47.11, 85, 86, 117; 191/12.2, 12.2 A

[56] References Cited

U.S. PATENT DOCUMENTS

| | | | |
|---|---|---|---|
| 3,120,355 | 2/1964 | Bowman | 242/54 R |
| 3,128,857 | 4/1964 | Walton | 191/12.2 |
| 3,222,002 | 12/1965 | Holberg | 242/54 R |
| 3,539,123 | 11/1970 | Shutt | 242/54 R |
| 3,545,693 | 12/1970 | Gurner et al. | 242/54 R |
| 3,822,834 | 7/1974 | Fjarlie | 242/54 R |

FOREIGN PATENT DOCUMENTS 872612 7/1961 United Kingdom ................. 242/54 R Primary Examiner—Leonard D. Christian
Attorney, Agent, or Firm—Cooper, Dunham, Clark, Griffin & Moran

[57] ABSTRACT

In computerized tomographic apparatus, in which a radiation source orbits through several revolutions about a patient, handling of cables can present a problem. This invention provides an arrangement for cable handling in which two cable stores have relative rotation. The cable is transferred, during rotation, from one to the other by a transfer means which also moves around the rotation axis.

8 Claims, 2 Drawing Figures

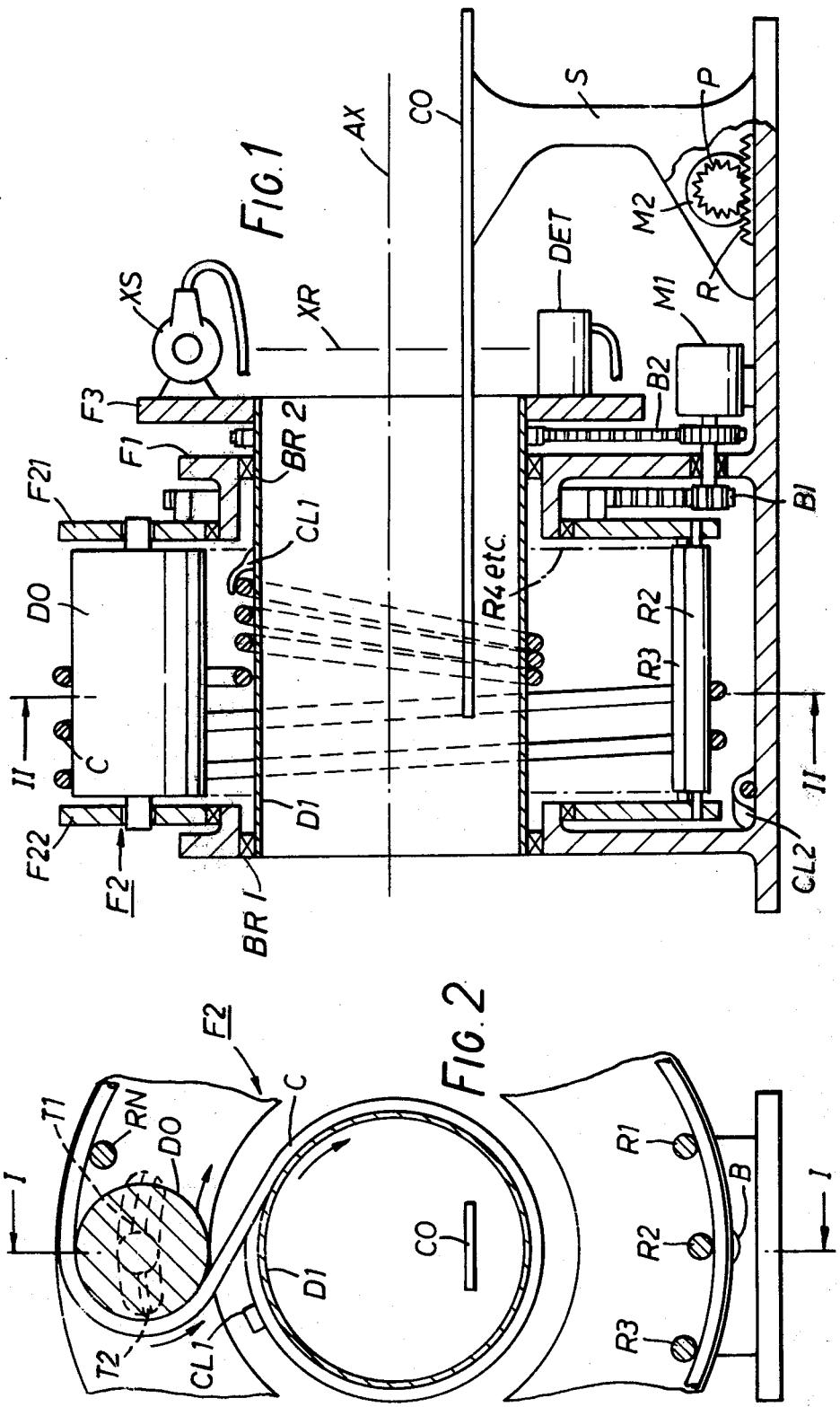

CABLE STORAGE ASSEMBLY FOR SCANNING APPARATUS

This invention relates to cable handling arrangements in computerised tomographic scanning apparatus.

Computerised tomographic apparatus often requires cable handling arrangements which permit some components of the apparatus (the radiation source, for example) to execute several revolutions around a patient. "Cables" as used herein includes single and multicore insulated electrical cables and also hoses for liquid or gas transfer. Clearly wear and tear of the cables should be kept to a minimum and preferably the handling arrangement is such that it can be enclosed by suitable covers to assist cleanliness and provide a restful appearance, both of which are desirable in a medical environment.

It has been proposed to allow the cable to form a loose loop drawn from and returned to a store. Such an arrangement can satisfactorily handle sufficient cable for one or two revolutions of the apparatus but does not have sufficient capacity to be conveniently used for a large number of revolutions.

It is an object of this invention to provide an improved cable handling arrangement for computerised tomographic apparatus which require several revolutions about the examining axis.

According to the present invention there is provided a cable handling arrangement for controlling a cable connecting two parts of an apparatus, one part being rotatable relative to the other part, the arrangement including: a first store arranged to hold a plurality of turns of the cable stationary relative to one of said parts; a second store arranged to hold a plurality of turns of the cable wound around the first mentioned turns and stationary relative to the other part; and transfer means, arranged to orbit about the axis of relative rotation intermediate the two pluralities of turns, effective to unwind the cable from one store and to wind it onto the other as the relative rotation progresses.

Embodiments of the invention will now be described with reference to the accompanying drawings in which:

FIG. 1 is a view in elevation of the invention showing a longitudinal sectional view along line I—I of FIG. 2 and, FIG. 2 is a transverse sectional view taken along line II—II of FIG. 1.

Referring to FIGS. 1 and 2 the X-ray machine has a main floor-standing frame member F1 supporting subsidiary frame members F2, F3 for revolution on an examination axis AX. A patient couch CO is also mounted on frame F1, by stand S, and is movable, e.g. by motor M2 and rack-and-pinion R and P shown in part only, along the axis AX. Frame member F3 supports an X-ray source XS and detectors DET which respectively project and detect X-rays XR transverse to axis AX to perform the examination.

The general operation of machines for such examination is now well-known and described in, for example, U.S. Pat. Nos. 3,778,614; 3,881,110 and 3,946,234 and further description will be related to the arrangement by which electrical, fluid pressure and other connections are made between the stationary frame member F1 and the frame member F3 by which the source XS and detector DET are revolved on axis AX through one or more, eg eight, revolutions.

The problem of providing reliable connections between a stationary and a revolving part of a machine is usually difficult to solve.

In particular X-ray machines for scanning examination require several types of cable connection ie high voltage, up to at least 100 KV, liquid or gas coolant circulation for the X-ray tube, low level control voltages and the outputs from the detectors such as DET. For reliability and acceptability in the medical use of the machine cables, hoses and the like flexible connectors are very suitable, avoiding open contacts, and it is possible to form a combined cable in which all the necessary feed paths are incorporated and which can be handled as a single item. However on considering the size of the machine the length of such a cable is seen to be large. Thus a cylindrical former or drum D1, arranged to hold the cable, must be large enough, about 600 to 1500 mm diameter, to receive within it a human body while for some examinations up to eight revolutions of the frame F3, connected to drum D1, are required.

Apparently, to allow eight revolutions of a drum such as D1, winding on a cable of which the other end is fixed, it is necessary to provide a cable length of at least eight times the circumference of the drum. It will be seen, however, that the length of cable required may be halved if the drum starts with the cable fully wound on it, proceeds through four revolutions in which the cable is fully unwound and then a further four revolutions in which the cable is rewound in the opposite sense. However that arrangement would still be inconvenient. First it will be apparent that at the midpoint of the rotation perhaps 10 meters of flexible cable would be fully unwound and this would be clearly inconvenient to be draped about the machine or to be contained in a storage loop as has been proposed for machines using less revolutions. Secondly the reversal of the sense of winding of the cable at the mid point of revolutions would require a comparatively rapid change of direction of the cable at the surface of the drum. The probable short bending radius and frequent changes of direction would then require extreme flexibility of the heavy cables used and would tend to reduce the life of the cable. This invention allows at least part of the advantage in cable saving given by an effective reversal of winding direction and does not cause a loose cable loop which needs to be accommodated.

One example of an arrangement of the invention can be seen in FIGS. 1 and 2 and that embodiment will now be described in detail. Drum D1 is supported on Frame F1 by suitable bearings, BR1 and BR2, which are spaced axially and carries at one end the frame F3 described above.

Drum D1 and frame F3 are driven to carry out the required examination.

Frame F2 is also supported on axially spaced portions of frame F1 and is drivable, to revolve about axis AX, by a motor M1 coupled to frame F2 by a toothed belt B1. Frame F2 has spaced cheeks, F21 and F22, which house between them a cage of small diameter rollers $R_1$, $R_2$, $R_3$ ... $R_N$ ... $R_n$ spaced at, say, 15° to 20° intervals to form in effect an outer cylindrical former or drum on which a cable C can be wound for transfer to drum D1. Cheeks F21, F22 also house one larger roller or drum, D0 which transfers cable C between the outer drum and drum D0. Drum D0 is sized to the smallest bending radius of cable C consistent with resonable life for the cable under repeated flexing around drum D0. One end of the cable C receives the necessary cables etc. from frame F3. It is then wound on the drum arrangement as follows. Towards the end at frame F3 the cable is clamped to drum D1 by a clamp CL1. It is then wound in one direction about D1, as shown in the Figures, for a few side-by-side turns, is then passed over drum D0 and would around the outer drum formed by rollers R1 to $R_n$ in the opposite direction for sufficient further turns to accommodate the desired rotation. The cable is then clamped to frame F1 at a clamp CL2. FIG. 2 shows the salient points of this winding. Means may be provided for maintaining tension in the cable, such as the spring loaded arrangement indicated at T1 operative on the axle of drum D0. A tension sensing means, indicated at T2 also operative on the axle of drum D0, may also be provided and linked to the control of motor M1 to regulate the tension in cable C.

In operation the cable C is transferred between the outer drum and drum D1 by drum D0, all being rotated by their respective drives. At the start of an examination most of the cable is wound around the drum associated with one frame, say the effective outer drum of rollers mounted on F2 for convenience. During the examination frame F3 is driven as required for the examination and cable C is wound around the surface of drum D1 as shown by the clockwise arrow in FIG. 2. The turns which have been wound on drum D1 revolve with that drum as constrained by clamp CL1. The effective outer drum of rollers R1 to Rn is however a stationary drum and the turns thereon remain stationary relative to frame F1 as restrained by clamp CL2.

It will be clear from FIG. 2 that, to allow the winding of turns onto D1 while the effective outer drum is stationary, the transfer point at drum DO must also move clockwise about axis AX, as shown in FIG. 2. Provided frame F2 was free to rotate the necessary orbit of drum D0 would of course be achieved by the pulling of the cable C. However to maintain a satisfactory tension in cable C frame F2 is driven by motor M1 in the same direction but at the slower speed necessitated by the pulley ratio of the system.

Rotation of frame F2 also orbits the individual rollers R about axis AX and, of course, orbits therewith the opening through which cable C is fed when passing over D0. The coil of C wound on rollers R do, however, remain stationary as desired, sliding over the rollers R which support them in a low friction manner, until they are pulled around D0 onto D1. The diameter of frame F2 at rollers R1 to Rn is greater than that of drum D1 so a few turns of frame F2 will permit a larger number of turns of drum D1.

In one machine drum D1 is some 650 mm in radius and the surface of the effective outer drum formed by rollers R1 to Rn is some 1000 mm in radius. Drum D0 is some 150 mm in radius. Drum D1 is to revolve eight times about axis AX. However drum D1 does not have to make eight revolutions with respect to frame F2, a lesser number being sufficient, as follows.

If the drum D1 makes $N_1$ turns with regard to frame F2 and the frame F2 makes $N_0$ turns with respect to the axis AX the total number of turns of the drum D1 about axis AX is $N_1 + N_0 = N_T$, (Eq.1). Let the radii of $D_1$ and the effective outer drum on F2 be $R_1$ and $R_0$ respectively. In the absence of slack the paid out cable, proportional to $R_o N_1$, (Eq.2). Setting $N_T = 8$, $R_1 = 650$ mm and $R_o = 100$ mm the simultaneous equations from equations 1 and 2 are solvable to give $N_1 = 4.85$, $N_o = 3.15$. Accordingly just over three turns of cable about the effective outer drum on frame F2 will permit eight revolutions of frame F3 about axis AX. Frame F3 proceeds at 8/3.15, i.e. 2.54× the speed of frame F2. The reverse action occurs when rewinding the cable.

It will be seen that a shorter length of cable is required with this arrangement than if the cable were simply wound onto drum D1 during eight revolutions in one direction and unwound on eight revolutions in the other direction, although slightly more than if the cable were unwound four turns and awkwardly reversed to wind four in the opposite direction.

The above calculation is based on the assumption that the surface of the effective outer drum, on the frame F2, supporting the cable is circular. In a practical form of the apparatus it may be desirable to use a triangular outer drum with drums such as D0 at each apex, such an arrangement being convenient to implement. It is also possible to use other polygons. The circular form may be provided by an apertured cylinder of material between the cheeks F21, F22 of frame F2 with a low friction coating e.g. PTFE if this does not cause too much drag on the cable.

As mentioned above, slack should be avoided during the transfer. By sensing the tension on the cable passing over drum D0, or elsewhere such as on the drum itself as described before, the speed of motor M1 can be regulated when transferring from the effective outer drum to drum D1 so that an increase in tension is relieved by an increase in the rate of revolution of frame F2 and vice versa. When transferring from drum D1 to the outer drum on frame F2 the reverse obtains. Suitable sensing and regulating arrangements to provide a controlled cable tension will be readily apparent.

If required drum D1 can be driven from frame F2 by fixed ratio gearing, for example epicyclic gear. Alternatively both can be driven by motor M1. In FIG. 1 drum D1, and frame F3, are driven by a toothed belt B2 and appropriate gearing. A spring load can then be applied to the slidingly supported drum D0 to maintain a selected tension.

The arrangement described provides cable handling for radiation scanning machines for various types in which the cable is under control and not subject to undue stress and in the illustrated embodiments permit the use of cable length shorter than would be required for simple loose storage between a drum and a fixed point without reversing the direction of winding.

What I claim is:

1. A cable handling arrangement for controlling a cable connecting two parts of an apparatus, one part being rotatable relative to the other part, the arrangement including: a first store means for holding a plurality of turns of the cable stationary relative to one of said parts; a second store means for holding a plurality of turns of the cable wound around the first mentioned turns and stationary relative to the other part; and transfer means orbiting about the axis of relative rotation intermediate the two pluralities of turns and including means to unwind the cable from one store means and to wind it onto the other store means as relative rotation of one of said parts relative to the other progresses.

2. An arrangement according to claim 1 in which the first store means comprises a cylinder which is stationary relative to the first mentioned part.

3. An arrangement according to claim 1 in which the second store means comprises an effective cylinder which is disposed around the first store.

4. An arrangement according to claim 3 including means for causing the second store means to rotate about the axis of relative rotation with the orbital motion of the transfer means to cause the second plurality of turns to move relative to the second store means and to remain stationary relative to said other part.

5. An arrangement according to claim 4 in which the second store means comprises a plurality of roller means disposed on the surface of the effective cylinder and mounted for rotation about respective axes parallel to the axis of relative rotation.

6. An arrangement according to claim 1 in which the transfer means comprises a drum mounted to rotate about an axis parallel to the axis of rotation and to orbit about said axis of relative rotation.

7. A cable handling arrangement for controlling a cable connecting two parts of an apparatus such as a scanning radiographic apparatus, relatively rotatable about a common axis, the arrangement including a first store means for holding a plurality of turns of the cable, wound in a first sense, stationary relative to one of said parts, a second store means for holding a plurality of turns of the cable wound in the opposite sense, stationary relative to the other part, and means operative in the course of relative rotation between said two parts of the scanning radiographic apparatus for progressively unwinding the cable from one store means and reversing and winding the cable onto the other store means, and transfer means for rotating about said axis relative to both parts and for transfering the cable, as it is reversed, from the one store to the other.

8. A cable handling arrangement, for a radiographic apparatus of which one part is arranged to rotate about an axis relative to another part, to control one or more cables connecting the two parts during said rotation, the arrangement including a first cable winding store means fixed relative to the first part for rotating therewith, a second cable winding store means effectively fixed relative to the second part and a cable transfer means for rotating about the axis with, and at a fixed speed ratio to, the first part, said cable being initially wound on one store in one sense and, as the rotation proceeds, said cable being removed by the transfer means from said one store and wound onto the other store in the opposite sense.

* * * * *

UNITED STATES PATENT AND TRADEMARK OFFICE
CERTIFICATE OF CORRECTION

PATENT NO. : 4,163,526
DATED : August 7, 1979
INVENTOR(S) : ANTHONY M. WILLIAMS

It is certified that error appears in the above-identified patent and that said Letters Patent are hereby corrected as shown below:

Page 1, left-hand column, delete:

"[30]  Foreign Application Priority Data
   Aug. 21, 1976 [GB] United Kingdom--------34938/76"

Column 2, line 38, after "of" and before "revolu-" insert -- the --.

Signed and Sealed this

Fifteenth Day of July 1980

[SEAL]

Attest:

SIDNEY A. DIAMOND

Attesting Officer

Commissioner of Patents and Trademarks